United States Patent [19]
Hickok et al.

[11] Patent Number: 5,657,541
[45] Date of Patent: Aug. 19, 1997

[54] HOLDER ASSEMBLY FOR SURGICAL BLADE

[75] Inventors: Teresa R. Hickok; Claude E. Martin, both of Chula Vista, Calif.

[73] Assignee: San Diego Swiss Machining Inc., Chula Vista, Calif.

[21] Appl. No.: 528,079

[22] Filed: Sep. 14, 1995

[51] Int. Cl.⁶ .................................................. B26B 5/00
[52] U.S. Cl. .................................. 30/123; 30/337; 81/439; 279/46.4; 279/56
[58] Field of Search .................... 30/337–339, 123; 206/363, 370; 81/437, 439; 279/46.4, 56

[56] References Cited

U.S. PATENT DOCUMENTS

| | | | |
|---|---|---|---|
| D. 324,475 | 3/1992 | Staubitz | D8/99 |
| 2,022,775 | 12/1935 | Holland-Letz | 81/439 |
| 4,496,163 | 1/1985 | Bernfeld | 279/46.4 X |
| 4,969,231 | 11/1990 | Mader et al. | 16/141 |
| 5,203,086 | 4/1993 | Dann | 30/293 |
| 5,433,457 | 7/1995 | Wright | 30/337 X |

FOREIGN PATENT DOCUMENTS 2201362  9/1988  United Kingdom ............... 279/46.4

*Primary Examiner*—Douglas D. Watts
*Attorney, Agent, or Firm*—Baker, Maxham, Jester & Meador

[57] ABSTRACT

A holder assembly for a surgical blade includes a handle assembly and a wrench for loosening/tightening the blade from/to the handle of the handle assembly. The handle assembly includes a collet having two longitudinal slits that enable the collet to secure the blade in a first and second direction to prevent slippage during operation. The collet fits in the handle and is secured by a retaining member that fits over the collet with the blade intact. The retaining member is loosened/tightened by a wrench that is part of the holder assembly. The wrench is configured to cover the blade completely when the wrench is placed in operation. Part of the cover is removable for cleaning by inserting the closed end of the wrench into the wrench body and pushing the cover's cap off.

21 Claims, 3 Drawing Sheets

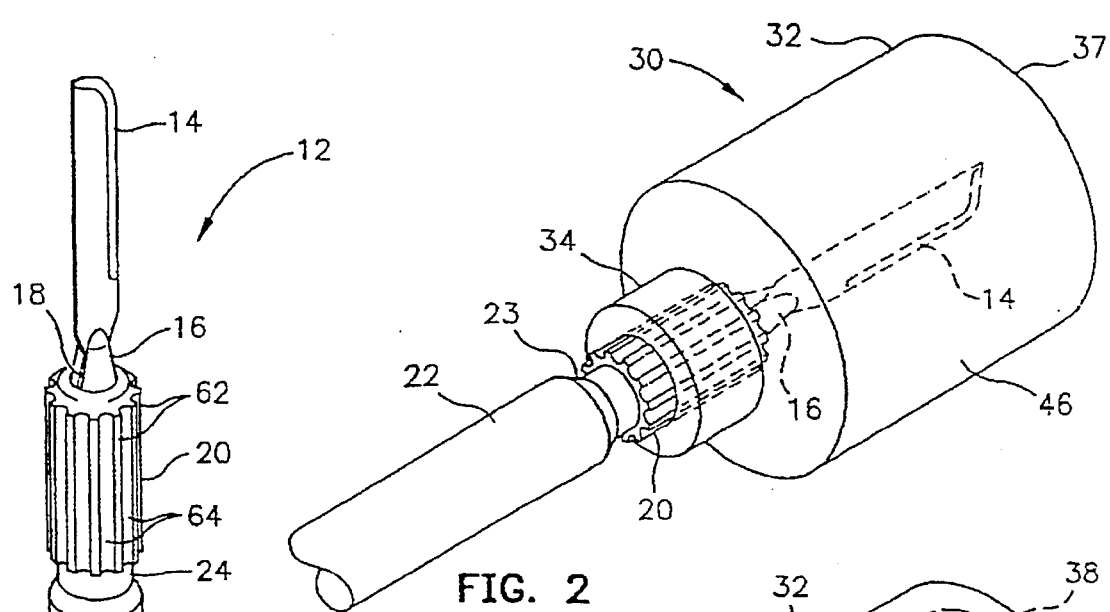
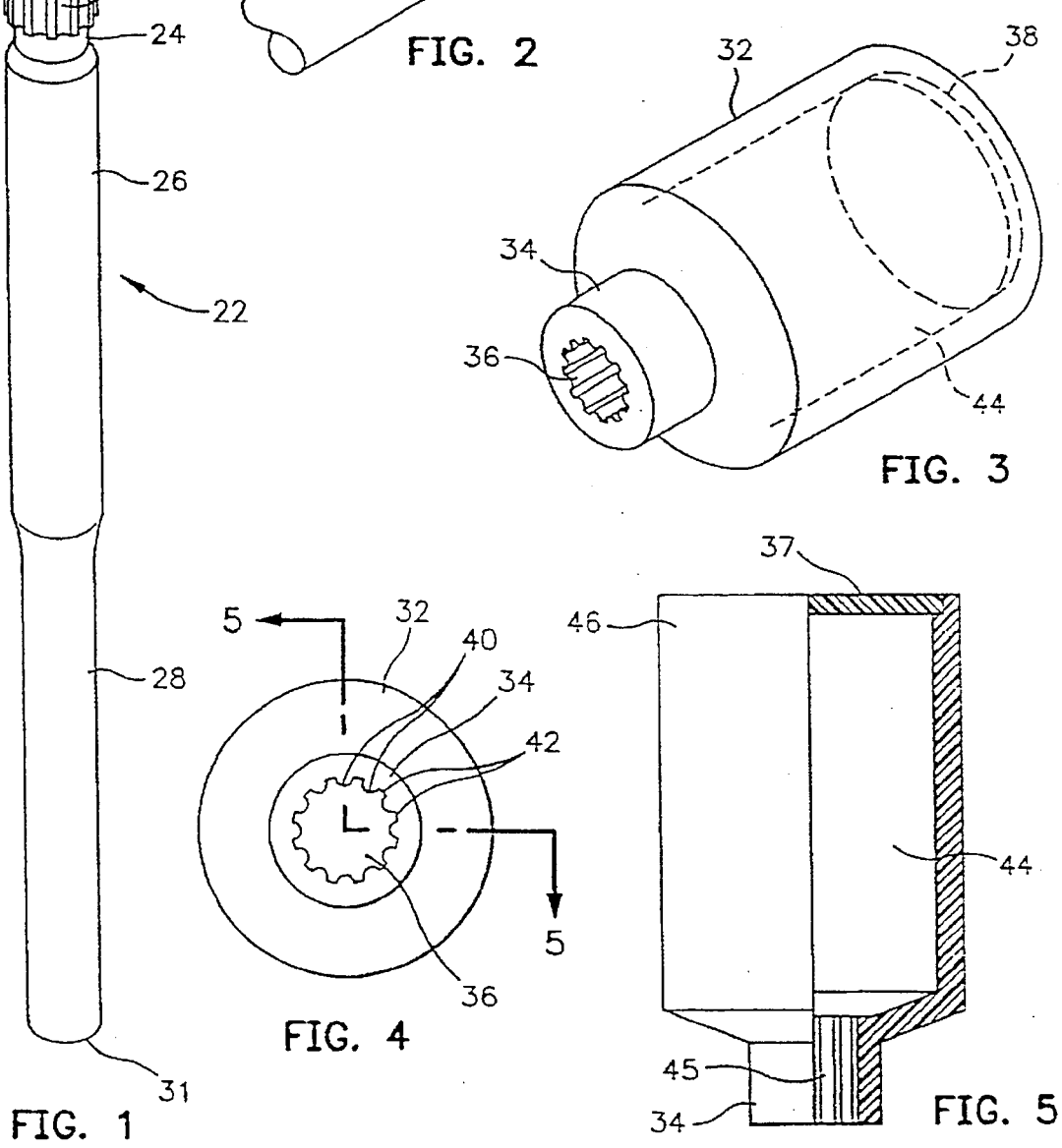

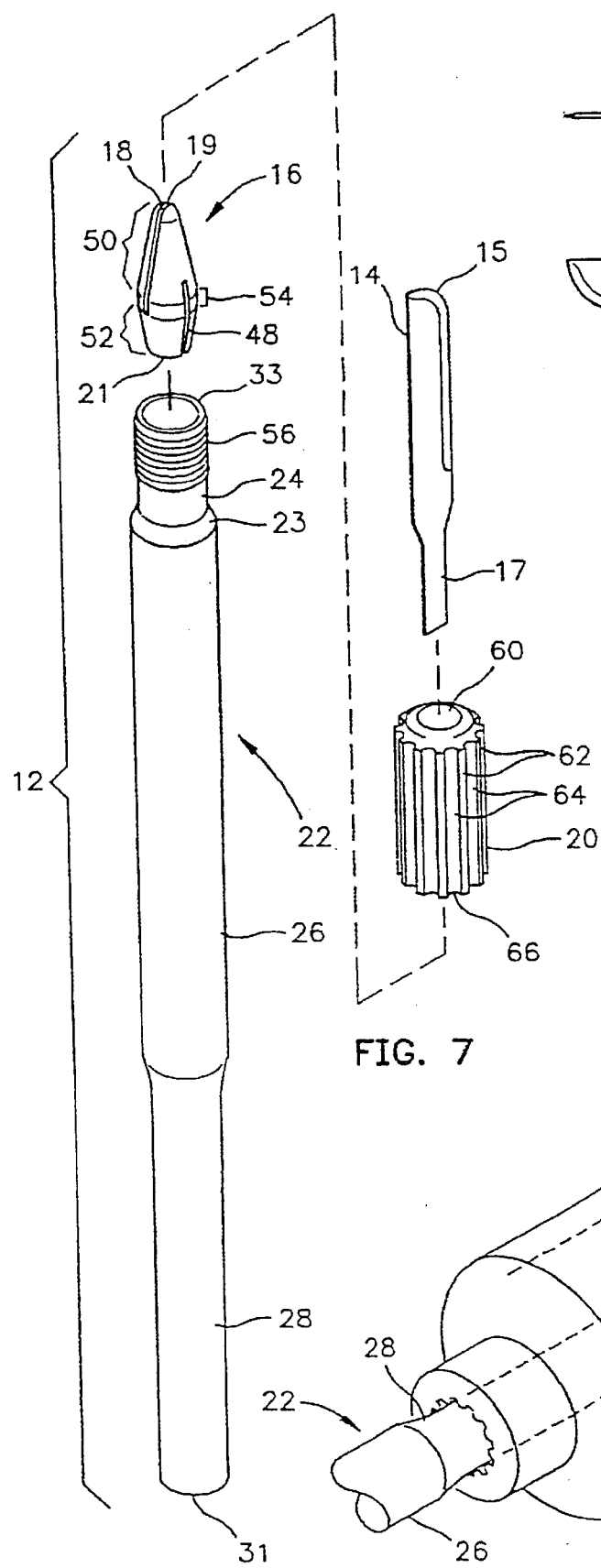
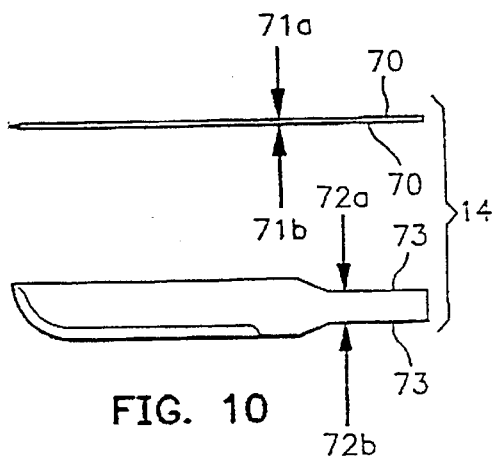
FIG. 10
FIG. 7
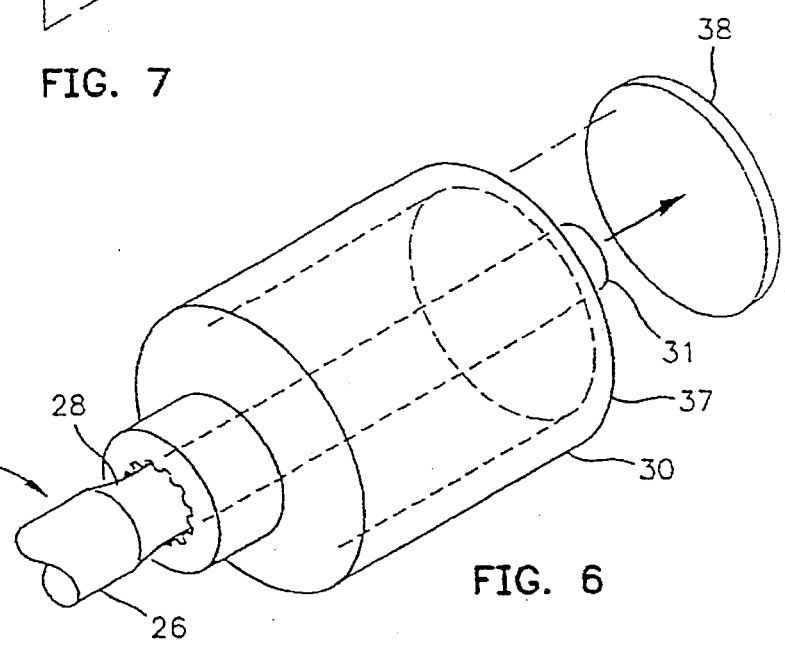
FIG. 6

HOLDER ASSEMBLY FOR SURGICAL BLADE

BACKGROUND OF THE INVENTION

1. Field of the Invention

This invention relates generally to surgical instruments and more specifically to an assembly for holding a surgical blade that improves the safety of using such blades.

2. Description of the Related Art

Surgical instruments and, in particular, blades are required to be extremely sharp in order to make incisions and the like. Unfortunately, the sharp instruments are a safety hazard to the people who use them. A cut to a doctor, nurse, or other medical personnel exposes the medical person to viruses and other infections that can enter the person's body through the open cut. Additionally, the cut may cause blood to contaminate the blade which exposes other persons, including patients, to the risk of exposure to these harmful contaminants.

Some viruses are lethal; for example, there is no known cure for infection by the Human Immunodeficiency Virus (HIV) that causes Acquired Immunodeficiency Syndrome (AIDS) and HIV is known to infect human blood. AIDS is a terminal condition, killing those who have acquired it by destroying the immune system so that the infected sufferer dies from AIDS related symptoms, such as pneumonia, that their body is unable to fend off. Because of the risk of such deadly infections, there is a long-felt need for medical instruments that are safe to clean and use.

One cause of injury by surgical tools is caused by a blade that is not securely held in place in its handle. Surgery tends to be very stressful on the cutting instrument due to odd cutting angles that are sometimes necessary and the force required to make an incision. Prior art surgical devices exhibit a tendency for the blade to be dislodged from its holder in such a situation. The inventors of the present invention have made the critical recognition that a significant factor contributing to this problem is that prior art surgical instruments hold the blade secure in only one direction. Thus, a substantial force introduced in another plane on the blade may dislodge it from its handle.

Another type of injury caused by sharp surgical blades occurs when the are being placed in or removed from their handles. Typically such blades are placed in a handle and a nut is tightened around a securing member to hold them in place. The nut is usually tightened with an open-end or boxed-end wrench. Any slippage by the operator, when tightening the nut, immediately exposes the operator to the risk of being cut by the sharp blade. A similar risk exists when the blade is being removed with such a wrench. What is needed is a wrench and blade handle assembly combination that allows for insertion/removal without exposing the operator to the risk of injury. Furthermore, such an advantage provided with a blade handle assembly that also prevents the slippage of such blades during operation would be a significant advancement in the art.

Because of the risk of exposure to contaminants in human blood, described above, it is essential that all instruments used in surgical operations be cleaned thoroughly before being re-used. Since a wrench used to remove the blade may become contaminated it must be cleaned after use. However, the inventors have made the critical recognition that there is a tension between the need to somehow shield the operator from the blade during insertion/removal and the need to clean the wrench because a wrench configured with extra parts for such prophylactic measures will be more difficult to clean than one that has no cover. Thus, it would be an advancement in the art to provide the advantages described above while enabling easy cleaning of the entire assembly including the wrench.

SUMMARY OF THE INVENTION

An objective of this invention is to provide an improved surgical blade holder that overcomes the problems described above. To meet this objective, and to this invention provides novel embodiments of a handle assembly tool to allow for safe installation/removal of blades from the assembly. The assembly includes a handle having an open end for receiving a collet configured to secure a cutting blade in two directions. The collet has longitudinal slits near the front and rear. The longitudinal slit near the front receives the blade into the body of the collet. A retaining member placed over the collet and turned in one direction compresses the collet including the slits. The compression of one slit causes gripping of the blade on opposing sides and the compression of the other causes gripping of the edges of the blade. One optional aspect of the invention is a combination of the handle assembly with a wrench and protective shield combination that enables removal/insertion of the collet and fits over the blade in the collet. The tool has a covered part that encloses the blade covering its sharp edges to prevent injury. Another portion of the wrench tool is configured to twist the retaining member in one direction for securing the blade and in an opposite direction for allowing removal of the blade. In a preferred embodiment, the wrench tool has a removably closed end disposed opposite an end that is configured to twist the retaining member. Other objects and advantages of this invention will be readily appreciated upon reading the following description in view of the accompanying drawings.

BRIEF DESCRIPTION OF THE DRAWING

The objects, advantages and features of the present invention will be more clearly understood by reference to the following detailed disclosure when read in conjunction with the accompanying drawing, in which:

FIG. 1 is a perspective view of the handle assembly of the present invention holding a blade having opposing sides and opposing edges;

FIG. 2 is an isometric view of a wrench for securing and loosening the retaining member of the handle assembly of FIG. 1 shown engaging the retaining member attached to the handle member of the handle assembly of FIG. 1;

FIG. 3 is an isometric view of the wrench of FIG. 2 with the handle assembly removed and a hidden view of the removable insert of the wrench shown;

FIG. 4 is a top plan view of the wrench of FIGS. 2 and 3 showing the open end for receiving the retaining member and blade of FIG. 1;

FIG. 5 is a partial sectional side view taken along line 5—5 of the wrench shown in FIG. 4;

FIG. 6 is an isometric view showing the removable insert of the wrench being removed by the closed end of the handle of FIG. 1;

FIG. 7 is an exploded view of the handle assembly of FIG. 1 showing the handle, the collet, the retaining member, and a blade;

FIG. 10 shows opposing sides and opposing edges of the blade of FIG. 1 with force vector shown to indicate the securing compressive forces enabled by the longitudinal slits of FIG. 8 and FIG. 9 when the collet is placed in the handle and the retaining member is turned in a securing direction.

DETAILED DESCRIPTION OF THE PREFERRED EMBODIMENT

Figure 8:
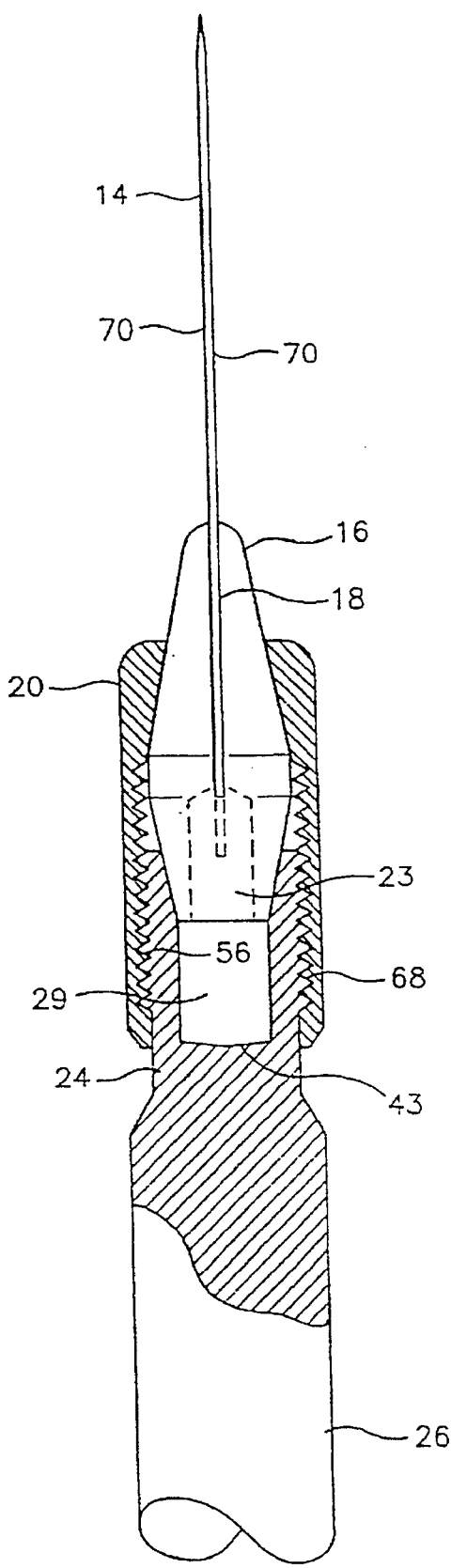
FIG. 8 is a partial sectional view of the collet secured in the handle by the retaining member and engaging a blade in a longitudinal slit.

This invention is described with reference to a preferred embodiment shown in the drawing figures. In these figures, a like number shown in various figures represents the same or similar elements in each figure. While this invention is described in terms of the best mode for achieving this invention's objectives, it will be appreciated by those skilled in the art that variations may be accomplished in view of these teachings without deviating from the spirit or scope of the invention.

Handle Assembly Overview

FIG. 1 shows a handle assembly designated generally by the numeral 12 for holding a blade 14 in a secure safe position. As will be described in detail below with reference to FIG. 7, the collet 16 holds the blade 14 secure in two directions gripping both opposing sides and opposing edges of the blade. Such a safe securing operation has not been achieved by the prior art and this is a novel non-obvious aspect of this invention. The collet 16 has a longitudinal slit 18 extending from one end of the collet for receiving the blade. When the collet 16 is compressed the opposing walls formed by slit 18 clamp down on the blade 14 and this provides one of the securing forces on the blade. The retaining nut or member 20 is used to tighten the collet and apply the compressive forces which allow the collet to hold the blade in place. The collet fits in an opening in the handle 22 and is secured by retaining member 20. Twisting the retaining member compresses the collet 16 and closes longitudinal slit 18 so that the blade is held in place. The handle member has a neck 24 near the first end which is open and a middle section 26 and a tapered portion 28 near the second end 31. It is not absolutely required that the portion 28 be tapered, i.e. of a smaller diameter than section 26. However, tapering this portion allows a portion of the handle to be thicker for a better grip for holding the blade while allowing some portion of the handle to be thinner so that it can be used in combination with a wrench member, described below, in order to remove a cap which fits over a normally closed end of the wrench.

Handle Assembly-Wrench Combination

Referring to FIGS. 2 and 3, a combined wrench and protective shield member 30 having an open end 36 and a closed end 37 is shown. FIG. 2 shows the wrench in operating engagement with the retaining member of the handle assembly which is in place on the neck portion of handle 22. The blade 14, held in place in the collet, is protectively contained or shielded within the axial passage 44 of the larger diameter portion 32 of the wrench 30. The blade is safely contained within the enclosure by cover 46. However, the blade can be safely loosened by wrench 30 for removal from handle 22 without exposing medical personnel to a sharp blade. The ability to loosen the blade or better secure it to the handle member without exposing the operator to the risk of an infection is believed to be a significant advancement in the art. A smaller cylinder portion 34 of the wrench body is configured to be able to apply a twisting force to retaining member 20. In turn this imparts a force on collet 16 and, in particular, compresses the longitudinal slits of the collet closer together to hold the blade firmly in place. Turning the wrench in an opposite direction loosens the retaining member 20, thereby allowing the longitudinal slits to expand and release blade 14.

FIG. 3 shows the opening 36 attached to the smaller cylinder portion 34 in which the retaining member fits to pass the blade into the axial passage of the wrench. At the second end 37 (FIG. 2) of the wrench a removable insert or cap 38 can be removed in order to allow cleaning of the axial passage 44 and the inside wall of cylindrical portion 34 which is configured to turn the retaining member 20. The cap is shown as a force-fit member, but it would be apparent to one skilled in the art to create threads on the cap and wrench member for allowing insertion and removal by a screwing action. This is a significant advancement in the art because it is important to clean any medical instrument which may have come into contact with blood due to the danger of contamination.

FIGS. 4 and 5 show the wrench 30 from a different point of view of that shown in FIG. 3. FIG. 4 is a top plan view of the wrench where opening 36 can be clearly seen. Ridges 40 and valleys 42, which are disposed between the ridges, are used for mating up with matching ridges 62 and valleys 64 (FIG. 1) on the retaining member 20 in order to twist the retaining member.

FIG. 5 shows a partial sectional view taken along sectional lines 5—5 of FIG. 4. In this view the cover 46 is partially removed to reveal the axial passage 44 and the inner wall 45 of the smaller cylindrical portion 32. In this view it will be appreciated that the end 37 is sealed by removable insert 38 so that the blade is not exposed. For safety's sake, it is important that the blade be prevented from jamming against the insert. This may be accomplished by shortening the length of the threaded portion of the smaller cylinder or by lengthening the longitudinal axis of axial passage 44.

FIG. 6 shows handle 22 with tapered portion 28 inserted in the axial passage of wrench 30 wherein end 31 is capable of pushing removable insert 38 off of end 37 of the wrench so that the inside of the wrench can be cleaned. The cleaning may be done in two steps, first with a bottle brush and then placing the wrench member in a sterilizing apparatus.

FIG. 7 shows an exploded view of the handle assembly 12 described above with reference to FIG. 1. The handle 22 includes open end 33 for receiving the collet and opposite closed end 31. Between the open end and the closed end is a neck 24 including a threaded portion 56, shoulder 23 which is adjacent middle portion 26, and tapered end portion 28 which is adjacent the closed end. The threads mate up with corresponding threads 68 (FIG. 8) on the inside of the retainer 20. The middle portion 26 is preferably thick enough to allow a comfortable grip by an operator. The reduced portion 28 is preferred to be dimensioned to fit within the axial passage of the wrench in order to pop the removable inset out.

The handle assembly includes a collet 16 that has a substantially elongated body that is preferably conically shaped at each end. The conically shaped body has a first longitudinal slit 18 extending from one end of the collet to substantially the middle 54 of the collet 16 forming a first pair of spaced opposed jaws. A second longitudinal slit 48 extends from an opposite end of the collet just past the middle portion 54 forming a second pair of spaced opposed jaws.

Preferably, the length of the slits overlap. Additionally, the slits should be offset at an angle from each other. In other words, each slit is offset at a different angle from the longitudinal axis. Preferably, each slit is offset at about ninety degrees from the other.

In a preferred embodiment, the conical shape is further divisible into two opposing cones sharing frustum sections through middle portion 54. The first conical section 50 has a tip at first end 19 and the oppositely oriented second cone 52 also has a frustum section in the middle 54 and has a somewhat truncated tip section at the end of the collet 21.

It is not necessary that the collet be conical in shape; however, the inventors have recognized that this is the best configuration for achieving the invention's objectives. The collet is preferably an elongated body having an axial passage from end 19 to end 21. The longitudinal slit 18 extends from end 19 to about the middle and receives the blade 14 into the axial passage of the collet. The opposing jaw or wall assembly formed by the longitudinal slit 18 is compressible by the retaining member at open end 60 so that the walls can be used to clamp or grip opposing sides of the blade. A second jaw or wall assembly formed by longitudinal slit 48 extends from the end 21 and is also compressible by the retaining member and serves to allow clamping or gripping by the inner walls of the collet of opposing edges of the blade. Thus the blade is gripped in two directions to ensure that it does not slip or fall out.

The ability to grip the blade in two directions is a critical advancement in the art which has not been accomplished by the prior art. It is preferable to place the blade into the collet prior to tightening the retaining member 20. Typically such blades, as blade 14, are provided with protective sheathes over sharp portion 15 which can be used by a human to grip the blade safely prior to placing it in the collet. However, these sheathes are disposed of once the blade is installed the first time, and subsequent removals are rendered dangerous with prior art wrenches.

A shank portion 17 of blade 14 slips into longitudinal slit 18 through an axial passage in the collet body and through open end 21. Blade 14 and collet 16 enter the retaining member 20 through open end 60. The retaining member is turned and its internal threads secure it to threads 56. Open end 66 of the retaining member, when installed on the assembly, extends past the threaded portion 56 into the neck portion 24 of the handle 22. Conveniently, the ridges 62 disposed on either side of valleys 64 can be used to turn the retaining member between the fingers of an operator. This hand-tightening operation is safe to perform the first time the blade is installed but the inventors have recognized that it is unsafe to perform by regular medical personnel once the sheath has been disposed and therefore have provided the wrench member for the combination of this invention. Once a retaining member including a collet and blade is removed from the handle it can be left in the protective enclosure of the wrench handle. The wrench member can then be moved to a special area where special equipment such as pliers are available so that specially trained personnel may process the contaminated blade. Meanwhile, a new blade, collet, and retaining member can be installed on the handle for use in surgery.

FIG. 8 is a partial sectional view showing a portion of handle 22 with the collet in place in the threaded portion of the neck of the handle and the retaining member also in place. Blade 14 is held in place in longitudinal slit 18 by the compressing force of retaining member 20 as the retaining member's threads 68 engage the threads 56. A hollow portion 29 in the neck begins at wall 43 and extends to end 33. It is partially filled up by the collet. The collet has an axial passage which is composed of hollow portion 23 of the collet combined with the longitudinal slit 18.

Figure 9:
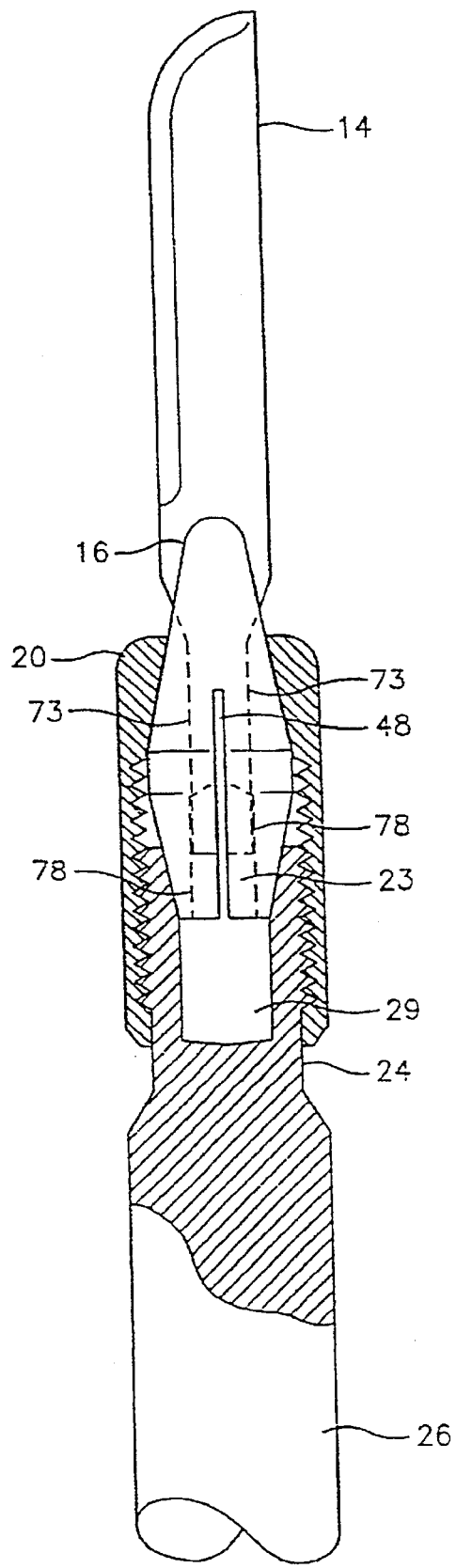
FIG. 9 is a partial sectional view of the collet, blade, retaining member and handle of FIG. 8 showing another longitudinal slit.

FIG. 9 shows a partial sectional side view of the handle, including middle portion 26 and neck 24, with the above-described threaded portion for mating with the threaded portion of the retaining member 20. When the retaining member is tightened the longitudinal slit 48 allows the inner walls 78 of the collet at hollow portion 23 to be compressed and clamped down on edges 73 of the blade 14. Thus, the blade is held in place by a securing compressive force on edges 73 as well as a securing compressive force in another direction on opposing sides 70 (FIG. 8). The longitudinal slits 18 and 48 allow the collet to be elastically deformable in response to a compressive force yielded by tightening the retaining member.

FIG. 10 shows a schematic representation of the compressive forces yielded by the collet on the blade 14. A compressive force in direction 71a and 71b on sides 70 is exerted by the compression of longitudinal slit 18. A compressive force in direction 72a and 72b on edges 73 is yielded when blade 14 is compressed by opposing jaws formed by the slit 48 as a result of axial force by the retaining member.

Regarding composition materials, the inventors have determined that the following choices are the best for achieving the invention's objectives. The wrench is preferably made of a sterilizable plastic, e.g. ultem. The collet is preferably made of stainless steel because of the desirable elasticity of that metal. Empirical evidence has shown that it is best to heat-treat the steel to obtain about 40–42 C-scale Rockwell hardness. The retaining member and handle are preferably made of titanium because it is very strong but is also light-weight and non-corrosive. The handle is preferably solid from end 31 to neck 24 until it is necessary to create the hollow portion for receiving the collet.

In view of the above description, it is possible that modifications and improvements will occur to those skilled in the art which are within the scope of the appended claims. Therefore, this invention is not to be limited in any way except by the appended claims.

What is claimed is:

1. A handle assembly for holding a blade having a generally rectangular cross sectional configuration with opposing substantially planar parallel sides and substantially planar parallel opposing edges, the assembly comprising:

a substantially elongate handle having first and second opposite ends, wherein the first end is open;

an elongated collet having a longitudinal axis and inner walls defining a substantially rectangular axial passage and first and second opposite ends, the collet having a first longitudinal slit extending from the first end for receiving a blade into the axial passage and forming a first set of opposed substantially planar parallel jaws that are compressible for gripping the opposing planar sides of the blade, and further having a second longitudinal slit extending from the second end and forming a second set of opposed substantially planar parallel jaws that are compressible for gripping opposing planar edges of the blade; and an elongated retaining member having first and second opposite open ends and a longitudinal axis with a longitudinal inner passage, the retaining member mounted at the first end of the handle and being configured to secure the collet and apply a compressive force to the collet, the retaining member having an inside surface and an outside surface.

2. The handle assembly of claim 1, wherein the collet is substantially conically shaped.

3. The handle assembly of claim 2, wherein the substantially conical collet is composed of two opposing cones each having a frustum and a tip, each frustum being adjacent to the other frustum and the tip of one cone being at the first end of the collet and the tip of the other cone being at the second end of the collet.

4. A combination for safely securing and loosening the retaining member to and from the handle assembly of claim 1, the combination comprising:

the handle assembly of claim 1; and a combined wrench and protective shield member, the wrench and protective shield member including:

a body having first and second opposite ends and a longitudinal axis and a covered axial passage for covering the blade; and the first end of the body being open for receiving the blade into the axial passage and having an inside surface that is configured to enable twisting of the retaining member in a first direction to secure the retaining member to the handle and in a second direction to loosen the retaining member from the handle.

5. A handle assembly for holding a blade having a opposing sides and opposing edges, the assembly comprising:

a substantially elongate handle having first and second opposite ends, wherein the first end is open;

an elongated collet having a longitudinal axis and inner walls surrounding an axial passage and first and second opposite ends, the collet having a first longitudinal slit extending from the first end for receiving a blade into the axial passage and forming a first set jaws that are compressible for gripping opposing sides of the blade, and further having a second longitudinal slit extending from the second end and forming a second set of jaws that are compressible for allowing the inner walls to grip opposing edges of the blade;

an elongated retaining member having first and second opposite open ends and a longitudinal axis with a longitudinal inner passage, the retaining member mounted at the first end of the handle and being configured to secure the collet and apply a compressive force to the collet, the retaining member having an inside surface and an outside surface;

a combined wrench and protective shield member, the wrench and protective shield member comprising:

a body having first and second opposite ends and a longitudinal axis and a covered axial passage for covering the blade; and the first end of the body being open for receiving the blade into the axial passage and having an inside surface that is configured to define coupling means for enabling twisting of the retaining member in a first direction to secure the retaining member to the handle and in a second direction to loosen the retaining member from the handle, wherein the second end of the combined wrench and protective shield member's body has a removable insert that can be removed in order to allow cleaning of the axial passage.

6. The combination of claim 5, wherein a portion of the handle near the second end of the handle is dimensioned to fit into the axial passage of the combined wrench and protective shield member so that the second end of the handle can be used to remove the removable insert of the body.

7. The combination of claim 4, wherein the retaining member of the handle assembly has outside surface ridges and valleys between the ridges.

8. The combination of claim 7 having inside surface ridges and valleys disposed near the first end and being keyed to match the corresponding ridges and valleys of the retaining member so that twisting the wrench twists the retaining member.

9. The combination of claim 4, wherein the combined wrench and protective shield member's body is composed of a first cylindrical portion having a diameter and a second cylindrical portion having a diameter, wherein the first cylindrical portion extends from the first end of the combined wrench and protective shield member to the beginning of the second cylindrical portion that extends to the second end of the combined wrench and protective shield member and the diameter of the second portion is greater than the diameter of the first portion.

10. The handle assembly of claim 1, wherein the retaining member has a threaded portion in the internal passage.

11. The handle assembly of claim 10, wherein the handle has a threaded portion at the first end for receiving the threaded portion of the retaining member.

12. A collet for a handle assembly configured to hold a blade having a generally rectangular cross sectional configuration with opposing substantially planar parallel sides and opposing substantially planar parallel edges, wherein the handle assembly has a substantially elongate handle having first and second opposite ends and the first end is open, the handle assembly further having a retaining member for securing the collet in the first open end of the handle, the collet comprising:

an elongated body having a longitudinal axis and inner walls defining a substantially rectangular axial passage and first and second opposite ends, the collet further having a first longitudinal slit extending from the first end for receiving a blade into the axial passage and forming a first set of opposed substantially planar parallel jaws that are compressible by the retaining member for gripping opposing sides of the blade, and further having a second longitudinal slit extending from the second end and forming a second set of opposed substantially planar parallel jaws that are compressible by the retaining member for gripping opposing edges of the blade.

13. The collet of claim 12, wherein the first longitudinal slit and the second longitudinal slit each extend from the respective first and second opposite ends such that the span of each slit overlaps the span of the other slit.

14. The collet of claim 12 wherein the first longitudinal slit is angular, displaces relative to the longitudinal axis and is offset by an angle from the second longitudinal slit.

15. The collet of claim 14, wherein the offset angle is ninety degrees.

16. A handle assembly for holding a blade having a generally rectangular cross sectional configuration with opposing substantially planar parallel sides and opposing substantially planar parallel edges, the assembly comprising:

a substantially elongate handle having first and second opposite ends, wherein the first end is open;

an elongated substantially conical collet having a longitudinal axis and inner walls defining a substantially rectangular axial passage and first and second opposite ends, the collet having a first longitudinal slit forming a first set of opposing substantially planar parallel jaws that are extending from the first end for receiving a blade into the axial passage and wherein the first set of jaws are compressible for gripping opposing sides of the blade, and further having a second longitudinal slit extending from the second end and forming a second set of opposing substantially planar parallel jaws that are compressible for gripping opposing edges of the blade; and an elongated retaining member having first and second opposite open ends and a longitudinal axis with a longitudinal inner passage, the retaining member mounted at the first end of the handle and being configured to secure the collet and apply a compressive force to the collet, the retaining member having an inside and an outside.

17. The handle assembly of claim 16, wherein the collet is composed of two opposing cones having adjacent frustums meeting near the center of the collet with each cone facing in opposite directions such that a tip of one cone is at the first end and a tip of the other cone is at the second end of the collet.

18. The handle assembly of claim 16, wherein the first longitudinal slit and the second longitudinal slit each extend from the respective first and second opposite ends such that the span of each slit overlaps the span of the other slit.

19. The handle assembly of claim 16, wherein the first longitudinal slit is angularly displaced relative to the longitudinal axis and is offset by an angle from the second longitudinal slit.

20. The handle assembly of claim 19, wherein the offset angle is ninety degrees.

21. A method for making a handle assembly for holding a blade having a generally rectangular cross sectional configuration with opposing substantially parallel sides and substantially parallel opposing edges, the method composing the steps of:

providing a substantially elongate handle having first and second opposite ends, wherein the first end is open;

providing an elongated collet having a longitudinal axis and inner walls defining a substantially rectangular axial passage and first and second opposite ends, the collet having a first longitudinal slit extending from the first end for receiving a blade into the axial passage and defining a first set of opposed parallel jaws, the first jaws being compressible for gripping opposing sides of the blade, and further having a second longitudinal slit extending from the second end and defining a second set of opposed parallel jaws, the second jaws being compressible for gripping opposing edges of the blade;

providing an elongated retaining member having first and second opposite open ends and a longitudinal axis with a longitudinal inner passage; and mounting the retaining member at the first end of the handle to secure the collet and apply a compressive force to the collet.

* * * * *